United States Patent
Rambach

(10) Patent No.: US 9,303,282 B2
(45) Date of Patent: Apr. 5, 2016

(54) SELECTIVE ENRICHMENT MEDIUM FOR CARBAPENEM-RESISTANT BACTERIA

(76) Inventor: Alain Rambach, Paris (FR)

( * ) Notice: Subject to any disclaimer, the term of this patent is extended or adjusted under 35 U.S.C. 154(b) by 489 days.

(21) Appl. No.: 13/055,169

(22) PCT Filed: Jul. 21, 2009

(86) PCT No.: PCT/EP2009/059346
§ 371 (c)(1),
(2), (4) Date: Jan. 21, 2011

(87) PCT Pub. No.: WO2010/010083
PCT Pub. Date: Jan. 28, 2010

(65) Prior Publication Data
US 2011/0129869 A1  Jun. 2, 2011

Related U.S. Application Data

(60) Provisional application No. 61/129,814, filed on Jul. 21, 2008.

(51) Int. Cl.
C12Q 1/02 (2006.01)
C12Q 1/04 (2006.01)
C12Q 1/10 (2006.01)

(52) U.S. Cl.
CPC . *C12Q 1/045* (2013.01); *C12Q 1/10* (2013.01)

(58) Field of Classification Search
None
See application file for complete search history.

(56) References Cited

U.S. PATENT DOCUMENTS 6,355,449 B1 * 3/2002 Chen et al. ............. 435/34
8,008,059 B1 * 8/2011 Roth et al. ............. 435/243

FOREIGN PATENT DOCUMENTS

FR       2 925 070        6/2009
WO    WO 2004/063391 A1   7/2004
WO    WO 2007/096639 A2   8/2007

OTHER PUBLICATIONS

Mudaliar, U.A., et al., "In Vitro Activity of Meropenem Compared to Nine Other Antimicrobial Agents: Importance of its Stability When Used in Agar Dilution Systems," *Pathology*, 1996, pp. 352-355, vol. 28(4).
Alhambra, A., et al., "In Vitro Susceptibility of Recent Antibiotic-Resistant Urinary Pathogens to Ertapenem and 12 Other Antibiotics", *Journal of Antimicrobial Chemotherapy*, vol. 53, (Apr. 2004), pp. 1090-1094.
Anderson, K.F., et al., "Evauulation of Methods to Identify the *Klebsiella pneumoniae* Carbapenemase in *Enterobacteriaceae*", *Journal of Clinical Microbiology*, vol. 45, No. 8, (Aug. 2007), pp. 2723-2725.
Bratu, Simona et al., "Emergence of KPC-Possessing *Klebsiella pneumoniae* in Brooklyn, New York: Epidemiology and Recommendations for Detection", *Antimicrobial Agents and Chemotherapy*, vol. 49, No. 7, (Jul. 2005), pp. 3018-3020.
Samra, Zmira, et al., "Evaluation of CHROMagar KPC for Rapid Detection of Carbapenem-Resistant *Enterobacteriaceae*", *Journal of Clinical Microbiology*, vol. 46, No. 9, (Sep. 2008), pp. 3110-3111.
Tamayo, J., et al., "Activity of Ertapenem and Other Antimicrobials Against ESBL-Producing Enterobacteria Isolated from Urine in Patients from Madrid", *Rev. Esp. Quimioterap.*, vol. 20, No. 3, (Sep. 2007), pp. 334-338.

* cited by examiner

*Primary Examiner* — Vera Afremova
(74) *Attorney, Agent, or Firm* — Alston & Bird LLP

(57) ABSTRACT

The present invention relates to a method for direct detection and differentiation of carbapenem-resistant bacteria in a sample comprising (i) inoculation with said sample of a culture medium comprising at least meropenem and/or ertapenem and at least one chromogenic agent, (ii) incubation of said culture medium under conditions allowing the growth of carbapenem-resistant bacteria, and (iii) detection of colonies formed on said culture medium corresponding to carbapenem-resistant bacteria, as well as a culture medium suitable for use in such a method.

4 Claims, No Drawings

SELECTIVE ENRICHMENT MEDIUM FOR CARBAPENEM-RESISTANT BACTERIA

FIELD OF THE INVENTION

The present invention relates to a method for specific and direct detection of carbapenem-resistant bacteria in a sample using a selective differential isolation medium for resistant bacteria comprising at least one carbapenem.

PRIOR ART

The carbapenems are a category of antibiotics obtained from *Streptomyces cattleya*. This is a family of antibiotics that is effective at low concentrations against the majority of Gram (−) bacteria, as well as against Gram (+) and anaerobic bacteria, including practically all beta-lactamase producing strains.

Various publications have reported the emergence of resistance to carbapenems in a wide variety of Gram (−) bacteria including *Pseudomonas aeruginosa, Burkholderia cepacia, Acinetobacter* species, *Proteus* species, *Serratia marcescens, Enterobacter* species and *Klebsiella pneumoniae*. This resistance to carbapenems can be highly transmissible.

Obviously, such resistance has serious implications for the treatment of bacterial infections with antibiotics from the carbapenem family insofar as bacterial resistance can lead to the failure of these treatments and epidemic transmission of this resistance. Identification of patient samples showing resistance to carbapenems and differentiation of various resistant strains is therefore particularly important because it can help limit the risk of treating a patient with unsuitable antibiotics. Thus, the risk of propagation of the infection can be limited by means of isolation techniques of infected patients and confinement of these strains by healthcare staff (special cleaning, use of gloves, dedicated medical materials and hospitalization).

It is therefore important to have available detection tools and methods for these bacteria which combine both good specificity and selectivity and, most importantly, ease of use such that tests can be simplified as much as possible, carried out quickly and in large numbers, and possibly even automated, in order to control hospital hygiene with regard to bacteria posing a nosocomial risk, at the same time as allowing rapid differentiation between various strains which might be resistant to carbapenems.

In the prior art, a microdilution technique was widely used for the detection of carbapenem-resistant bacteria but this is currently under question in view of the number of false positive results to imipenem found by several studies (CARMELI et al., *Journal of Clinical Microbiology*, vol. 36, p: 595-597, 1998; GRIST, *Journal of Clinical Microbiology* 30:535-536, 1992). Given this, the technique that mainly used at the present time is that of diffusion discs which requires, similarly to microdilution, preliminary isolation of the strain whose resistance or not to carbapenem is to be tested, thus requiring very tedious application within the scope of systematic hospital monitoring.

Overall, the current methods of detection consist of two successive steps in order to allow specific detection of carbapenem-resistant bacteria: isolation on a non-selective and non-differential medium followed by analysis of sensitivity to various antibiotics. This means a fairly long period of time for screening and diagnosis, thus increasing the risk of the spread of multi-resistant bacteria in treatment centres and the risk of error. Moreover, these detection methods do not make it possible to differentiate between various strains which might be resistant to carbapenems.

Thus, there is presently a considerable need for a simple, more specific, more direct, faster detection technique which also allows various carbapenem-resistant bacterial strains to be differentiated but which does not require a combination of several consecutive tests, leading to further delays in obtaining results and increasing the risk of parasitic contamination or error as well as the risk of the spread of multi-resistant bacteria in treatment centres.

SUMMARY OF THE INVENTION

The present invention relates to a method for direct detection of carbapenem-resistant bacteria in a sample comprising the following successive steps:

a) Inoculation with said sample of a culture medium comprising at least meropenem and/or ertapenem and at least one chromogenic agent, b) Incubation of said culture medium under conditions allowing the growth of carbapenem-resistant bacteria, and c) Detection of colonies formed on said culture medium corresponding to carbapenem-resistant bacteria.

Another object of the present invention relates to a culture medium suitable for use in said detection method.

DESCRIPTION OF THE INVENTION

Surprisingly and unexpectedly, the inventor has shown that use of meropenem and/or ertapenem in place of imipenem makes it possible, in chromogenic differential media, to limit false positive results for the detection of carbapenem-resistant bacteria and to directly detect carbapenem-resistant bacteria, at the same time as differentiating between them and obtaining species identification information. In particular, when carried out on a solid agar medium, the detection method developed by the inventor can be carried out directly on a patient sample without the need for a preliminary isolation step of the different strains present in a sample.

In particular, the method of the invention can be applied to the detection of carbapenem-resistant strains of the KPC+ bacteria type which carry the KPC gene.

Consequently, a first object of the present invention consists in a method for the direct detection of carbapenem-resistant bacteria in a sample comprising the following successive steps:

a) Inoculation with said sample of a culture medium comprising at least meropenem and/or ertapenem and at least one chromogenic agent, b) Incubation of said culture medium under conditions allowing the growth of carbapenem-resistant bacteria, and c) Detection of colonies formed on said culture medium corresponding to carbapenem-resistant bacteria.

Advantageously, the method according to the present invention moreover comprises a step d) allowing the presence or not of a particular bacterial strain to be ascertained as a function of the colour of the colonies formed.

Compared to previous methods, the method developed by the inventor allows direct and rapid detection of carbapenem-resistant bacteria as well as immediate differentiation of various carbapenem-resistant strains by means of chromophore (s) released or not by the chromogen(s). In parallel, meropenem and ertapenem respectively show very good or good stability in an agar medium (2 to 4 months) and the detection method according to the invention has shown that, in such a medium, the detection method can be carried out effectively over several months.

In fact, meropenem has shown an important and unexpected stability.

Preferably, the antibiotic used to apply the detection method is meropenem. Generally, carbapenem-resistant bacteria belong to the following genera: *Pseudomonas* (e.g., *Pseudomonas aeruginosa*), *Burkholderia* (e.g., *Burkholderia cepacia*), *Acinetobacter, Proteus, Serratia* (e.g., *Serratia marcescens*), *Enterobacter, Klebsiella* (e.g., *Klebsiella pneumoniae*) or *Escherischia* (e.g., *Escherischia coli*).

Preferably, "carbapenem-resistant bacteria" means bacteria containing a gene coding for a beta-lactamase which hydrolyses carbapenems of the KPC family (*Klebsiella pneumoniae* carbapenase) such as KPC-1 (e.g., *Klebsiella pneumoniae*, access number: AAG13410), KPC-2 (e.g., *Klebsiella pneumoniae*, access number: AAK70220), KPC-3 (e.g., *Klebsiella pneumoniae*, access number: AAL05630), KPC-4 (e.g., *Klebsiella pneumoniae*, access number: ACA34343), KPC-5 (e.g., *Pseudomonas aeruginosa*, access number: ABY91240), KPC-6 (e.g., *Klebsiella pneumoniae*, access number: ACB71165).

The term "direct detection method" means a method which does not include a preliminary isolation step of the various bacterial strains present in the sample, preferably a method which does not include a preliminary isolation step of each of the bacterial strains present in the sample.

In fact, the method of the invention avoids the isolation step for bacterial colony candidates which can then undergo a more precise test to confirm their carbapenem-resistance status. It therefore applies to the raw sample comprising a mixture of bacteria.

The term "sample" means a mixture of different bacterial strains belonging to different species, or even different genera. As an example, said sample corresponds to a mixture of at least two different bacterial strains, preferably at least five different bacterial strains and, more preferably, to at least ten different bacterial strains.

Said sample advantageously corresponds to a liquid biological sample such as saliva, blood or urine, or a solid sample such a faeces, or equally to a derivative of a liquid or solid biological sample (faeces, etc) such as a pre-culture of such a liquid or solid biological sample.

Advantageously, said sample is a liquid or solid biological sample.

The term "chromogenic agent" means a compound with a chromophore released after hydrolysis by a specific enzyme of a particular bacterial genus or species.

The use of chromogenic agent in the medium permits to differentiate between various strains which might be resistant to carbapenems.

By "differentiate", one should understand that the color(s) obtained by the release or non-release of (a) chromophore(s) on the strain detected on the medium permits to distinguish between various strains which might be resistant to carbapenems, as illustrated in the following examples.

For example, the enzymes whose activity can be used within the scope of the present invention includes: β-D-glucuronidase or β-D-galactosidase, positive in *Escherischia coli*; β-D-glucosidase, positive in *Klebsiella, Enterobacter, Serratia* and *Citrobacter*; and/or desaminase, positive in *Proteus, Providencia* and *Morganella*.

Preferably, said chromogenic agent(s) carries a chromophore released after hydrolysis by a specific enzyme of a species or genus selected from the group consisting of: *Pseudomonas* (e.g., *Pseudomonas aeruginosa*), *Burkholderia* (e.g., *Burkholderia cepacia*), *Acinetobacter, Proteus, Serratia* (e.g., *Serratia marcescens*), *Enterobacter, Klebsiella* (e.g., *Klebsiella pneumoniae*) and *Escherischia* (e.g., *Escherischia coli*).

Alternatively, the chromogenic agents can be chosen to allow differentiation of different clones of the same species rather than species or genus differentiation. As an example, chromogens can be chosen which make it possible to distinguish between different *Klebsiella pneumoniae* clones which infect the same hospital, in order to carry out epidemiological monitoring of these clones within the scope of hospital hygiene and gradual eradication. With regard to the chromophores whose release is to be obtained by means of application of one or more enzymatic activities of one or more strains of the micro-organisms to be detected, the following can be cited: O-nitrophenyl, P-nitrophenyl, ChloroNitrophenyl, Hydroxyphenyl, Nitroanilide, Phenolphthalein and Thymophthalein, Hydroxyquino line, Cyclohexenoesculetine, Dihydroxyflavone, Catechol, Resazurin, Resofurin, VBzTM, VLM, VLPr, VQM, Indoxyl, 5-bromo-4-chloro-3-indoxyl, 5-bromo-6-chloro-3-indoxyl, 6-chloro-3-indoxyl, 6-fluoro-3-indoxyl, 5-lodo-3-indoxyl, N-Methylindoxyl, or other (refer to BIOSYNTH. or GLYCOSYNTH catalogue, www.biosynth.com and www.glycosynth.co.uk).

Preferably, the cenzymatic substrate of the chromogenic agent is selected in the group consisting in beta-D-glucopyranoside and beta-D-galactopyranoside, or a combination thereof, and more preferably the chromogenic agent is selected in the group consisting in 1-O-Methyl-beta-D-glucopyranoside, o-nitrophenyl-beta-D-glucopyranoside, 5-bromo-4-chloro-3-indolyl-beta-D-glucopyranoside, 4-methylumbelliferyl beta-D-galactopyranoside, 5-bromo-6-chloro-3-indolyl beta-D-galactopyranoside, 2-nitrophenyl-beta-D-galactopyranoside, 4-nitrophenyl-beta-D-galactopyranoside, N-Methyl indolyl-beta-D-galactopyranoside, 5-iodo-3-indolyl-beta-D-galactopyranoside, beta-trifluoromethyl-umbelliferyl-beta-D-galactopyranoside and indolyl-beta-D-galactopyranoside.

Preferably, said culture medium is an agar culture medium, wherein the culture medium is, for example, agar-based.

Meropenem and ertapenem are well known compounds to the man skilled in the art and can be obtained from MOLEKULA Ltd, for example.

The effective quantity of meropenem and/or ertapenem which is selective for carbapenem-resistant bacteria can be quite simply established by the man skilled in the art from his general knowledge and the results described in the examples below.

Advantageously, meropenem concentration is between 0.25 and 2 mg/L, preferably between 0.3 and 1 mg/L and, and more preferably, between 0.35 and 0.8 mg/L.

Advantageously, ertapenem concentration is between 0.5 and 2 mg/L, preferably between 0.8 and 1.5 mg/L and, and more particularly, between 0.9 and 1.2 mg/L. The incubation conditions allowing the growth of carbapenem-resistant bacteria are well known to the man skilled in the art and are not different from the usual methods.

Moreover, the culture medium used in the method of the invention can advantageously include at least one substance which reacts specifically with a particular bacterial genus.

For example, the culture medium used in the method of the invention can include deoxycholate which kills Gram (+) strains, preferably at a concentration of 0.8 to 1.2 g/L and/or amphotericin which kills yeasts, preferably at a concentration of 3 to 7 mg/L, and even more preferably from 4 to 6 mg/L.

Preferably, the culture medium used in the method according to the present invention is a CHROMagar Orientation medium (BD DIAGNOSITC SYSTEM) comprising at least one antibiotic chosen from among meropenem and ertapenem or a combination thereof.

A second object of the invention relates to a culture medium likely to be applied in a direct detection method of carbapenem-resistant bacteria in a sample such as that described previously.

Advantageously, said culture medium is an agar medium.

Advantageously, the antibiotic used in the culture medium of the present invention is meropenem.

A third object of the invention relates to the use of a culture medium such as that described previously for the direct detection and differentiation of carbapenem-resistant bacteria.

The following examples are given for the purpose of illustration only and in no way limit the extent of the present invention.

EXAMPLES

1) Tests on Meropenem Versus Imipenem to Select Carbapenem-resistant Bacteria

Different strains of carbapenem-sensitive bacteria or carbapenem-resistant bacteria were cultured under three sets of conditions:
  group 1: CHROMagar Orientation medium
  group 2: CHROMagar Orientation medium in the presence of meropenem (0.065; 0.25; 1 or 4 mg/L); and
  group 3: CHROMagar Orientation medium in the presence of imipenem (MSD, TIENAM (includes 50% imipenem) 0.0325; 0.125; 0.5 or 2 mg/L of imipenem)

The results show that the minimum concentration of meropenem (0.25 mg/L) to eliminate carbapenem-sensitive flora is about ten times lower than the necessary minimum concentration of imipenem (1 mg/L).

2) Ageing Tests on Meropenem Versus Imipenem to Select Carbapenem-resistant Bacteria Different strains of carbapenem-sensitive bacteria or carbapenem-resistant bacteria were cultured under three different sets of conditions and with different spreading concentrations:
  group 1: CHROMagar Orientation medium
  group 2: CHROMagar Orientation medium in the presence of imipenem (MSD, TIENAM (includes 50% imipenem) 1 or 2 mg/L imipenem), and
  group 3: CHROMagar Orientation medium in the presence of meropenem (0.12 or 0.25 mg/L).

Culture plates were then incubated at 37° C. and analysed regularly to establish the growth or absence of growth of bacteria.

The results showed that at a concentration of 2 mg/L of imipenem, inhibition of the growth of carbapenem-sensitive bacteria after 55 days in culture was similar to that obtained at a concentration of 1 mg/L after 21 days in culture. The results also confirmed that meropenem is much more effective than imipenem in terms of inhibition and that after 55 days in culture, the inhibition of the growth of carbapenem-sensitive bacteria at 55 days in culture in the presence of 0.25 mg/L of meropenem is always higher than inhibition obtained at a concentration of 0.12 mg/L of meropenem after 36 days in culture.

Finally, the results unexpectedly show that meropenem is a much more effective candidate for the selection of carbapenem-resistant bacteria than imipenem, but more especially that meropenem also has much higher stability in the used culture medium compared to imipenem.

3) Tests on Ertapenem to Select Carbapenem-resistant Bacteria

Different strains of carbapenem-sensitive bacteria or carbapenem-resistant bacteria were cultured under two sets of conditions:
  group 1: CHROMagar Orientation medium; and
  group 2: CHROMagar Orientation medium in the presence of ertapenem (INVAZ; 0.0325; 0.065; 0.125; 0.25; 0.5 or 2 mg/L).

The results show that the minimum concentration needed to eliminate carbapenem-sensitive flora falls between that of meropenem and imipenem.

4) Direct Detection of Carbapenem-resistant Bacteria Using Meropenem

Various urine samples from patients suffering from bacterial infections were taken.

Said samples were added directly to Petri dishes with CHROMagar Orientation agar medium, which contains two chromogens substrates, i.e. beta-D-glucopyranoside and beta-D-galactopyranoside, in the presence of 0.25 mg/L meropenem.

After incubation for 18 to 24 hours, visual analysis of the Petri dishes allowed direct identification of dishes containing bacteria.

The results are given in the table below:

| Species | Colour of colony |
|---|---|
| E.coli | Red |
| Klebsiella | Metallic blue |

Thus, the method of the invention makes it possible, in a single culturing step, to specifically detect and differentiate carbapenem-resistant bacteria without the need for a preliminary isolation step or subsequent differentiation step.

The invention claimed is:

1. A method for direct detection of carbapenem-resistant bacteria in a biological sample that comprises a mixture of different bacterial strains, said method comprising the following successive steps:
  a) inoculating a culture medium with said sample, wherein the culture medium comprises a single antibiotic and at least one chromogenic agent wherein said chromogenic agent is sensitive to the activity of at least one enzyme selected in the group consisting of β-D-glucuronidase, β-galactosidase, β-D-glucosidase, and a deaminase, and wherein the antibiotic is meropenem at a concentration between 0.25 and 2 mg/L,
  b) incubating said culture medium under conditions allowing the growth of carbapenem-resistant bacteria, and
  c) detecting colonies formed on said culture medium corresponding to carbapenem-resistant bacteria,
  wherein said method does not include a preliminary isolation step of the different bacterial strains present in said biological sample;
  wherein said chromogenic agent is hydrolysed into a chromophore selected from a group consisting of O-nitrophenyl, P-nitrophenyl, ChloroNitrophenyl, Hydroxyphenyl, Nitroanilide, Phenolphthalein, Thymophthalein, Hydroxyquinoline, Cyclohexenoesculetine, Dihydroxyflavone, Catechol, Resazurin, Resofurin, VBzTM, VLM, VLPr, VQM, Indoxyl, 5-bromo-4-chloro-3-indoxyl, 5-bromo-6-chloro-3-indoxyl, 6-chloro-3-indoxyl, 6-fluoro-3-indoxyl, 5-Iodo-3-indoxyl, and N-Methylindoxyl; and,
  said carbapenem-resistant bacteria are selected from the group consisting of the following genera: *Pseudomonas*,

*Burkholderia, Acinetobacter, Proteus, Serratia, Enterobacter, Klebsiella* and *Escherischia*.

2. The method according to claim 1, wherein said bacteria are bacteria containing a gene coding for a beta-lactamase which hydrolyses carbapenems of the KPC Family (*Klebsiella pneumoniae* carbapenase).

3. The method according to claim 1, wherein said culture medium is an agar culture medium.

4. The method according to claim 1, wherein said culture medium contains meropenem at a concentration between 0.35 and 0.8 mg/L.

* * * * *